United States Patent [19]
Richards et al.

[11] 3,988,429
[45] Oct. 26, 1976

[54] KIT FOR THE RAPID PREPARATION OF $^{99M}$Tc RED BLOOD CELLS

[75] Inventors: Powell Richards, Bayport, N.Y.; Terry D. Smith, St. Ann, Mo.

[73] Assignee: The United States of America as represented by the United States Energy Research and Development Administration, Washington, D.C.

[22] Filed: Apr. 16, 1975

[21] Appl. No.: 568,809

[52] U.S. Cl. .............................. 424/1; 252/301.1 R; 23/258.5 R
[51] Int. Cl.$^2$ ................... A61K 29/00; A61K 43/00
[58] Field of Search .................. 424/1; 252/301.1 R; 23/253

[56] References Cited
UNITED STATES PATENTS
3,725,295   4/1973   Eckelman et al. ............ 252/301.1 R OTHER PUBLICATIONS
Smith, International Journal of Applied Radiation and Isotopes, vol. 25, No. 3, Mar., 1974, pp. 137–139.

American Journal of Roentgenology, Radium Therapy and Nuclear Medicine, vol. 118, No. 4, Aug., 1973, pp. 861–864.

*Primary Examiner*—Benjamin R. Padgett
*Assistant Examiner*—Christine M. Nucker
*Attorney, Agent, or Firm*—Dean E. Carlson; Leonard Belkin

[57] ABSTRACT

A method and sample kit for the preparation of $^{99m}$Tc-labeled red blood cells in a closed, sterile system. A partially evacuated tube, containing a freeze-dried stannous citrate formulation with heparin as an anticoagulant, allows whole blood to be automatically drawn from the patient. The radioisotope is added at the end of the labeling sequence to minimize operator exposure. Consistent 97% yields in 20 minutes are obtained with small blood samples. Freeze-dried kits have remained stable after five months.

4 Claims, No Drawings

KIT FOR THE RAPID PREPARATION OF $^{99M}$TC RED BLOOD CELLS

BACKGROUND OF THE INVENTION

The invention described herein was made in the course of, or under a contract with the U.S. Atomic Energy Commission and/or its successor the Energy Research and Development Administration.

Labeled red blood cells (RBC's) have historically been used for imaging of the blood pool, including the placenta and for red cell mass determinations. Damaged labeled cells have been used for spleen imaging, and more recent applications have included blood pool dynamics and cardiac blood pool imaging, in which it is important to use imaging radiopharmaceuticals that are retained in the vascular system.

However, the application of $^{99m}$Tc-labeled RBC's has been limited by the need to withdraw and label a sample of the patient's blood just prior to clinical study—a laborious task with existing labeling methods. Earlier preparation methods in which no reducing agents were used resulted in minimal success. Reductive methods using stannous ion produced the first dependable labeling method (see U.S. Pat. No. 3,725,295), but yields were limited to the 50–60% range which made it necessary to separate the unbound $^{99m}$Tc before the labeled cells were injected. In later efforts, improved yields were achieved by decreasing the stannous ion content, but these systems required the preparation of fresh solutions just before use and considerable handling, sometimes including washing steps.

SUMMARY OF THE INVENTION

The present invention overcomes the problems mentioned above by providing a simplified and reproducible method and reagent kit for carrying out the method described in U.S. Pat. No. 3,725,295 relating to the use of the stannous ion in the labeling of RBC's and the present invention consistently produces high labeling yields with few mechanical steps.

In accordance with a preferred embodiment of this invention, there is provided a method of labeling red blood cells with $^{99m}$Tc comprising the steps of supplying a sample of the blood to a previously prepared partially evacuated container having within a dry mixture of an anticoagulant and a reagent for supplying a stannous ion, dissolving the dry mixture in the blood followed by adding a sterile saline solution, centrifuging the solution to form a layer of packed red blood cells and removing some of the latter, and mixing the removed red blood cells with a previously prepared saline solution of Na $^{99m}$TcO$_4$.

In accordance with another preferred embodiment of this invention, there is provided a kit for use in the labeling of red blood cells with $^{99m}$Tc comprising a partially evacuated container having a needle for receiving a blood sample, the container having within under sterile conditions a dry mixture of sodium heparin, stannous citrate in microgram amounts, sodium citrate, and dextrose.

It is thus a principal object of this invention to provide for the convenient and efficient preparation of $^{99m}$Tc-labeled red blood cells.

Other objects and advantages of this invention will hereinafter become obvious from the following description of preferred embodiments of this invention.

DESCRIPTION OF THE PREFERRED EMBODIMENTS

A kit prepared for use in accordance with the principles of this invention consists of a reagent tube containing the dried reagents sodium heparin, stannous citrate including the stannous ion, sodium citrate, and dextrose.

The reagent tube is a sealed unit equipped with a hypodermic needle made sterile, and partially evacuated to draw the amount of blood desired. Such tubes are available commercially, and one such tube, found to be useful, is the Vacutainer, a registered trademark of Becton-Dickinson.

The sodium heparin is a well known anticoagulant and is used in sufficient amount required for the size of the blood sample to be taken. The sodium citrate and dextrose provide bulk in the kit and serve to prevent hydrolizing of the tin, that is, they act as metal chelate stabilizers.

The reagents for the kit are prepared as follows:

In one flask, the stannous citrate is dissolved in an aqueous solution of sodium citrate-dextrose. It is preferable to dissolve the stannous citrate in a very small amount of the diluent first and then add more diluent as this seems to be more effective in keeping the tin in solution.

In a second flask, sodium heparin is dissolved in the same diluent and an aliquot from the first flask is added. The solution in the second flask is filtered into the reagent tube and then frozen. The reagent tube with its frozen contents is then freeze-dried followed by stoppering in situ under evacuated conditions. Although aseptic procedures are followed terminal sterilization of the stoppered reagent tube by radiation from a $^{60}$Co source at 2.5 megrads is preferred.

The reagent tube is employed in the following manner to label red blood cells with $^{99m}$Tc:

A sample of the patient's blood is drawn through the hypodermic needle into the tube. The amount of vacuum present determines the size of the sample. The contents of the tube are then mixed gently at ambient temperature until the reagents are all dissolved, usually only a few minutes.

Sterile saline is added to the tube, mixed, and then centrifuged to form a layer of packed red blood cells against the stopper. Some of the red blood cells are then removed through the use of a special needle and the red blood cells removed are then transferred to a vial in which there is a previously prepared saline solution of Na $^{99m}$TcO$_4$. The technetium-RBC mixture is incubated and mixed gently at room temperature for a few minutes and then diluted for injection.

The aqueous solution of sodium citrate and dextrose optimally should contain ½% by weight of the citrate and ¾% by weight of the dextrose. Maximum amounts are 1% for each of these stabilizers. In the kit, this results in a range of above 0.08 to 0.56 mg of sodium citrate for each ml of the blood sample. The dextrose, which acts as a filler, would typically be employed in amounts up to approximately two or three times the amount of the sodium citrate.

The amount of stannous ion employed in the stock solution is critical as the yield of labelled blood falls off sharply above and below the critical amount. The critical amount of stannous ion is found to be in the range of about 0.10 to 0.25 μg of stannous ion per 1 ml of the blood sample to be taken. The optimum level is found to be about 0.17 μg per ml of blood.

The saline solution added to the blood sample is for the purpose of dilution and the amount to be added is not critical.

It will be noted that the packed red blood cells are added to a solution of sodium pertechnetate containing $^{99m}$Tc. The radioactive technetium is obtained by means of an elution process using a generator system now well known in the art. The pertechnetate ion obtained consists of a mixture of the $^{99m}$Tc and the ground state $^{99}$Tc as the latter is a daughter product of the 6 hour half-life former. It has been found that in carrying out this invention that while the amount of pertechnetate solution is not critical, the amount of $^{99}$Tc present is a critical factor. For any size solution, the sodium pertechnetate solution containing a mixture of $^{99}$Tc and $^{99m}$Tc should not contain a total of more than 1000 disintegrations per minute of $^{99}$Tc. Ordinarily, the activity of the solution is determined from the history of the solution, i.e., how long ago the sodium pertechnetate was obtained from the generator and the amount of solution. The amount of $^{99m}$Tc required is determined by the medical application to be carried out.

Among the advantages of method and kit herein described is that the kit with its dried reagents has a long shelf life and the pertechnetate ion need be added only as required. Furthermore, labeling yields of 97% are consistently achieved by this method. In addition, the invention makes it possible to label small volumes of blood which is useful in certain applications where only small volumes can be employed. Also, smaller blood samples ordinarily will mean less trauma to the patient.

A fuller and even detailed description of the kit and method described herein is given in our paper "A Sample Kit for the Preparation of $^{99m}$Tc-Labeled Red Blood Cells" (BNL 19564) issued by the Brookhaven National Laboratory, and the contents of said paper are incorporated herein.

EXAMPLE

All glassware and equipment were washed with soap, rinsed with distilled water, then rinsed in 10% HCl, and finally rinsed in distilled water. Cleaned glassware was drained, wrapped in aluminum foil, and sterilized in a hot air oven at 190° C for 3 hours. The final formulation was dispensed into 10-ml Vacutainer (TM of Becton-Dickinson) tubes that had been disassembled and prepared as the other glassware had been. The Vacutainer rubber stoppers were washed by the same procedure but were not sterilized. Rubber stoppers, when autoclaved, tended to retain moisture, even after vacuum drying. The moisture escaped slowly from the stoppers into the dried formulation during storage significantly shortening the shelf life of the kits. To circumvent this difficulty, stoppers were washed as before, but were not autoclaved before use, and a terminal radiation sterilization was included in the kit preparation.

Stannous citrate solutions were prepared in an aqueous citrate-dextrose diluent (for the freeze-dried kit, dextrose was substituted for the sodium chloride in the diluent) containing 1.0 g of sodium citrate and 1.5 g of dextrose per 200 ml of solution as follows:

a. Stannous Citrate Concentrated Solution—6.5 mg of stannous citrate (initially dissolved on the glassine weighing paper in 3 drops of a solution of 1 ml citrate-dextrose diluent plus 4 ml saline) was diluted to 50 ml with citrate-dextrose diluent.

b. Stannous Citrate Diluted Solution—Sodium heparin (10,000 units in 1 ml, Upjohn) was dissolved in about 20 ml of citrate-dextrose diluent in a second 50-ml volumetric flask and 2 ml of Stannous Citrate Concentrated Solution (a) added. The dilution was made up to volume with citrate-dextrose diluent.

The filling operation was conducted in a Model VBM-400 Baker Laminar Flow Hood cleaned with 70% isopropyl alcohol before each filling operation. All filling equipment and materials were swabbed with alcohol before transfer to the hood. Half-milliliter aliquots of the Stannous Citrate Diluted Solution (b) were filtered from an all-glass system (modified 25-ml buret) through an 0.22-μm Millipore filter into the sterile Vacutainer tubes. A slight positive nitrogen pressure was used to force the solution through the filter. Filled tubes were transferred to an aluminum block (3 × 8.5 × 8.5 inches with holes to accept 100 × 15/16 mm tubes), the block was surrounded with dry ice, and the samples were frozen. Using sterile forceps, clean slotted rubber stoppers were inserted loosely into the tubes, with a vent left for vapor escape, and a thin aluminum plate was placed on top of the stoppers to provide even pressure during final stoppering at the end of the freeze-drying process.

The block containing the frozen samples was transferred to a modified Model 10-800 Virtis Freeze-Dryer (shelf temperature precooled to about −40° C). After evacuation of the chamber to 10–30 μ Hg, the samples were lyophilized for 36 hours at a shelf temperature of 40° C (105° F). The freeze-dried chamber was then backfilled to 16 inches Hg with nitrogen, and the tubes were remotely stoppered in situ. Tubes stoppered under these conditions automatically drew 6 ml of whole blood from the patient. The correct partial vacuum was determined by stoppering several tubes under different partial vacuums and testing their blood-draw volumes on animals. Tubes stoppered at 9.5 inches Hg drew 3 ml of whole blood. The finished product was terminally sterilized by radiation from a $^{60}$Co source (2.5 megarads). A representative fraction of the final kits was tested for both sterility and the presence of pyrogens, as well as for RBC labeling efficiency.

DESCRIPTION OF KIT COMPONENTS:

1 sterile disposable Vacutainer needle multiple sample, 20 G, 1½ inches
1 Vacutainer adapter
1 20 G, 9/32 inch hypodermic needle (special)
1 Vacutainer reagent tube, 100 × 15/16 mm, 10 ml capacity, evacuated to draw 6 ml whole blood and containing
100 units of sodium heparin
2.6 μg stannous citrate (1.0 μg stannous ion)
2.5 mg sodium citrate
3.7 mg dextrose.

PROCEDURE FOR USING THE BNL RBC KIT TO PREPARE $^{99m}$Tc-LABELED RBC'S

Use aseptic techniques throughout the procedure.
1. Add 1–5 ml of saline pertechnetate to a sterile and pyrogen-free 15-ml pharmaceutical vial and assay. IMPORTANT: Determine the maximum $^{99m}$Tc activity for satisfactory performance of the kit. The technetium atoms added to the kit must not exceed the number of atoms of technetium ($^{99m}$Tc plus $^{99}$Tc) generated by the decay of 10 mCi of $^{99}$Mo. Store in a lead shield.

2. The Vacutainer tube as supplied is evacuated to draw about 6 ml of whole blood. Draw the patient's blood sample into the Vacutainer using a sterile 20 G, 1½ inches multiple sample Vacutainer needle and Vacutainer adapter.

3. Mix immediately to dissolve the freeze-dried solids in the blood and gently mix the tube contents 5 min at room temperature.

4. Add 4 ml of sterile saline to the blood. CAUTION: To avoid pressure buildup in the Vacutainer tube, draw 4 ml of sterile saline into a 10-ml syringe, push the hypodermic needle through the Vacutainer stopper, and, with the tube upright so that blood will not be drawn back into the syringe, pull the syringe plunger back to the 8-ml mark. Allow the created vacuum to draw the saline into the tube.

5. Mix briefly, and centrifuge the tube upside down for 5 min at 1300 G.

6. Maintain the tube in the inverted position to avoid disturbing the packed RBC's. Withdraw 2 ml of RBC's using a 20 G, 9/32 inch needle. NOTE: The needle length has been adjusted to just penetrate the stopper.

7. Transfer the RBC's to the premeasured technetium prepared in step 1.

8. Incubate the technetium-RBC mixture for 5 min at room temperature, with gentle mixing.

9. Assay and dilute appropriately for injection.

Cell separation and yield determination at this point consistently give 97% yields.

What is claimed is:

1. The method of labeling red blood cells with $^{99m}$Tc comprising the steps of
   a. supplying a sample of blood to a container having therein an anticoagulant, a freeze-dried stannous reagent consisting of stannous citrate present in the range of about 0.10 to 0.25 µg of the stannous ion for each ml. of the blood sample, and a metal chelate stabilizer to provide bulk;
   b. incubating the resulting mixture until all of the solids are dissolved;
   c. adding sterile saline solution;
   d. centrifuging the contents of said container to form packed red blood cells;
   e. withdrawing some of said packed red blood cells;
   f. mixing said packed red blood cells with previously prepared saline solution of Na$^{99m}$TcO$_4$; and
   g. incubating the technetium-red blood cells mixture with gentle mixing.

2. The method of claim 1 in which the anticoagulant is sodium heparin.

3. The method of claim 2 in which the metal chelate stabilizer includes sodium citrate and dextrose.

4. A kit for use in the labeling of red blood cells with $^{99m}$Tc comprising a partially evacuated container with a needle for the insertion of a blood sample, said container having within under sterile conditions a dry mixture of sodium heparin, stannous citrate in the amount of about 0.10 to 0.25 µg of stannous ion per ml. of blood sample to be taken, sodium citrate, and dextrose.

* * * * *